(12) United States Patent
Von Bergen et al.

(10) Patent No.: US 12,357,214 B2
(45) Date of Patent: Jul. 15, 2025

(54) ECG ELECTRODE ATTACHMENT DEVICE

(71) Applicant: Wisconsin Alumni Research Foundation, Madison, WI (US)

(72) Inventors: Nicholas Von Bergen, Middleton, WI (US); Matthew Knoespel, Madison, WI (US); Philip Terrien, Madison, WI (US); Frank DeGuire, Brookfield, WI (US); Joseph Macksood, Appleton, WI (US); Andrew Budde, Hartland, WI (US); Alexi Harrod, White Bear Lake, MN (US)

(73) Assignee: Wisconsin Alumni Research Foundation, Madison, WI (US)

( * ) Notice: Subject to any disclaimer, the term of this patent is extended or adjusted under 35 U.S.C. 154(b) by 806 days.

(21) Appl. No.: 17/203,378

(22) Filed: Mar. 16, 2021

(65) Prior Publication Data
US 2021/0290136 A1 Sep. 23, 2021

Related U.S. Application Data

(60) Provisional application No. 62/990,532, filed on Mar. 17, 2020.

(51) Int. Cl.
*A61B 5/30* (2021.01)
*A61B 5/274* (2021.01)
*A61B 5/282* (2021.01)

(52) U.S. Cl.
CPC ............ *A61B 5/282* (2021.01); *A61B 5/274* (2021.01); *A61B 5/303* (2021.01); *A61B 2562/222* (2013.01)

(58) Field of Classification Search
CPC ......... A61B 5/274; A61B 5/282; A61B 5/303; A61B 2562/222; A61B 5/6823;
(Continued)

(56) References Cited

U.S. PATENT DOCUMENTS 4,353,372 A * 10/1982 Ayer .................. H01R 12/7076
174/268
5,813,979 A * 9/1998 Wolfer ................... A61B 5/303
600/508
(Continued)

FOREIGN PATENT DOCUMENTS

JP H0638938 * 4/1991

OTHER PUBLICATIONS

"Sure-Lock Electrode Clip." Curbell Medical, Feb. 16, 2019, curbellmedical.comsure-lock-electrode-clip. (Year: 2019).*

*Primary Examiner* — Eun Hwa Kim
*Assistant Examiner* — Dana Stumpfoll
(74) *Attorney, Agent, or Firm* — Boyle Fredrickson, SC

(57) ABSTRACT

A set of precordial electrodes are pre-attached along a single electrical cord where the electrodes can adjust in separation distances to accommodate different sizes of patients without cord looping or tangling. The invention employs cord corrals that permit a distance between adjacent electrodes to be shortened or lengthened while organizing excess cord. By allowing the adjacent electrode connectors to be shortened or lengthened, the lead array of electrode connectors may be used on a variety of different patient demographics and body sizes. While the single electrical cord eliminates the need for individual attachment of each of the lead wires of each of the electrodes to the ECG monitor.

17 Claims, 4 Drawing Sheets

(58) Field of Classification Search
CPC ....... A61B 5/28; A61B 5/6833; A61B 5/6884; A61B 18/1233; A61B 18/1445; A61B 18/1206; A61B 2017/00725; A61B 2018/00595; A61B 2018/00601; A61B 2018/00827; A61B 2018/00892; A61B 2018/00898; A61B 2018/0072; G01R 31/52

See application file for complete search history.

(56) References Cited

U.S. PATENT DOCUMENTS

| | | | |
|---|---|---|---|
| 6,205,355 B1* | 3/2001 | Lomanto | A61B 5/303 600/509 |
| 2006/0286861 A1* | 12/2006 | Avevor | A61B 5/303 439/501 |
| 2008/0281180 A1* | 11/2008 | Choe | A61B 5/282 600/391 |
| 2009/0247854 A1* | 10/2009 | Bordon | B65H 75/42 600/344 |
| 2011/0077497 A1* | 3/2011 | Oster | A61B 5/259 600/300 |
| 2011/0092833 A1* | 4/2011 | Farrior | A61B 5/318 600/508 |
| 2011/0270100 A1* | 11/2011 | Chang | A61B 5/0006 600/509 |

* cited by examiner

ECG ELECTRODE ATTACHMENT DEVICE

CROSS REFERENCE TO RELATED APPLICATIONS

This application claims the benefit of U.S. Provisional Patent Application No. 62/990,532, filed Mar. 17, 2020, which is incorporated by reference herein in its entirety.

STATEMENT REGARDING FEDERALLY SPONSORED RESEARCH OR DEVELOPMENT

N/A

BACKGROUND OF THE INVENTION

The present invention relates to electrocardiogram (ECG) systems and, more specifically, to attachment systems for ECG electrodes to ECG monitors that allow for the management of ECG lead wires therebetween.

An ECG is a common diagnostic tool used by hospitals to measure faint electrical signals in the heart to diagnose a disease or condition. In 2015, over 40 million ECGs were conducted by physicians in the United States alone.

The ECG utilizes electrodes that are placed on the skin at specific locations on the body. ECG lead wires are attached to the electrodes which relay the signal to an ECG monitor which will produce a display of an ECG waveform (e.g., T wave, QRS complex, and P wave) used by a physician to diagnose and treat the patient.

Currently, in order to obtain a standard precordial (chest) 12-lead ECG reading on a patient, the ECG technician must place ten or more electrodes on specific parts of the patient's body-one electrode on each of the arms (left arm, "LA" and right arm, "RA"), one electrode on each of the legs (right leg, "RL" and left leg, "LL"), and six electrodes across the patient's chest (fourth intercostal space at the right sternal border, "V1", fourth intercostal space at the left sternal border, "V2", halfway between leads V2 and V4, "V3", fifth intercostal space in the midclavicular line, "V4", left anterior axillary line on the same horizontal plane as V4, "V5", and left midaxillary line on the same horizontal plane as V4 and V5, "V6"). The technician then attaches wires with clips or snaps to each of these electrodes, each wire running from the electrode to the ECG monitor and which relay individual electrode readings to the monitor.

This process can be time-consuming, as the technician sorts through wires, and can create the risk of faulty readings if the technician mis-connects the clips to the electrodes. Electric clips that are loose or become dirty can introduce resistance that can obscure the faint ECG signal or introduce noise or in an extreme case fall from the patient's body.

SUMMARY OF THE INVENTION

The present invention provides a set of precordial electrodes pre-attached along a single electrical cord where the electrodes can adjust in separation distances to accommodate different sizes of patients without cord looping or tangling. The invention employs cord corrals that permit a distance between adjacent electrodes to be shortened or lengthened while organizing excess cord. By allowing the adjacent electrode connectors to be shortened or lengthened, the lead array of electrode connectors may be used on a variety of different patient demographics and body sizes. While the single electrical cord eliminates the need for individual attachment of each of the lead wires of each of the electrodes to the ECG monitor.

Specifically, in one embodiment, the invention provides an assembly for connecting a set of electrocardiogram (ECG) leads between electrodes on a patient to an ECG monitor receiving cardiac signals through the set of ECG leads, comprising: a set of electrode connectors fixed with respect to each other along an axis wherein each of the electrode connectors is electrically connectable to the surface electrodes on the chest of the patient; a set of wire corrals extending between the set of electrode connectors, the set of wire corrals permitting a spacing between the electrode connectors to be independently adjustable; and at least one individually insulated electrical conductor extending along the axis and physically interconnecting the set of electrode connectors and electrically communicating individual cardiac signals to the ECG monitor.

It is thus a feature of at least one embodiment of the present invention to provide a single sheath apparatus allowing for a tangle free corralling of electrode wires between patient electrodes and an ECG monitor. It is also a feature of at least one embodiment of the present invention to utilize the same device on patients of different body sizes.

A plurality of surface electrodes may have a male metallic snap fastener element connectable to the set of electrode connectors and a pad contacting the patient's skin.

It is thus a feature of at least one embodiment of the present invention to be able to use the apparatus with standard metal ECG electrodes placed on the skin of the patient's chest.

The plurality of electrical conductors may be physically interconnected with the other electrode connectors but electrically separate from the other electrode connectors.

It is thus a feature of at least one embodiment of the present invention to corral the multiple electrode wires along a single track that avoids cord looping or tangling.

The plurality of electrical conductors may be an integrated insulated sheath extending along an array axis. The single electrical connector may be a ribbon cable.

It is thus a feature of at least one embodiment of the present invention to eliminate the multiple connections of loose electrode wires making for easier set up and less confusion.

The set of electrode connectors may comprise housings supporting an electrical connection between the electrodes on the patient and the at least one electrical conductor.

It is thus a feature of at least one embodiment of the present invention to provide connection hubs associated with each electrode connector greatly simplifying the association of the electrode connector with the proper electrode.

The set of wire corrals may be expansion joints configured for corralling the at least one electrical conductor therein. The expansion joints are expandable and compressible along a longitudinal axis of the expansion joints and moveable perpendicular to the longitudinal axis with the ends of the expansion joint offset from each other.

It is thus a feature of at least one embodiment of the present invention to permit the distance between electrode connectors to adjustable vary while keeping their physical connection intact.

The set of wire corrals may be rotating spools configured for winding the at least one electrical conductor around the spools. The rotating spool may have a slip ring wherein a stationary electrical contact from an electrode of the patient electrically communicates with the rotating slip ring. The at least one electrical conductor may be mechanically attached to the spool and electrically connected to the slip ring.

It is thus a feature of at least one embodiment of the present invention to permit intuitive lengthening and shortening of the electrical conductor through a commonly known retraction device.

The spools may further include a constant force spring. The spools may include a rim of teeth interacting with a spring-loaded finger that engages with the teeth.

It is thus a feature of at least one embodiment of the present invention to allow for the retraction of the electrode wires without excessive force or weight being placed on each electrode connector.

The set of wire corrals may be a winding device such as seat belt retractors.

It is thus a feature of at least one embodiment of the present invention to provide an easy to clean and reusable device.

The set of electrode connectors may include at least seven electrode connectors connected to a RA electrode and V1-V6 electrodes, respectively.

It is thus a feature of at least one embodiment of the present invention to utilize the apparatus with standard 12 lead electrodes.

The set of electrode connectors may comprise a clip connectable to an ECG electrode on the patient. The clip may be a Sure-Lock locking metal clip. The clip may be an alligator clip.

It is thus a feature of at least one embodiment of the present invention to use the apparatus with common preexisting clip or snap type electrodes.

The at least one electrical conductor may be connectable to a trunk cable which is further connectable to the ECG monitor.

It is thus a feature of at least one embodiment of the present invention to use the apparatus with common preexisting trunk cables.

In one embodiment, the invention provides a method of connecting a set of electrocardiogram (ECG) leads between electrodes on a patient to an ECG monitor receiving cardiac signals through the set of ECG leads, comprising: arranging an assembly comprising a set of electrode connectors fixed with respect to each other along an axis wherein each of the electrode connectors is electrically connectable to the surface electrodes on the chest of the patient; wherein the assembly further comprises a set of wire corrals extending between the set of electrode connectors, the set of wire corrals permitting a spacing between the electrode connectors to be independently adjustable and a plurality of individually insulated electrical conductors extending along the axis and physically interconnecting the set of electrode connectors and electrically communicating individual cardiac signals to the ECG monitor on a chest of a patient; and connecting the electrodes on the patient to the set of electrode connectors.

These particular objects and advantages may apply to only some embodiments falling within the claims and thus do not define the scope of the invention.

DETAILED DESCRIPTION OF THE PREFERRED EMBODIMENT

Figure 1:
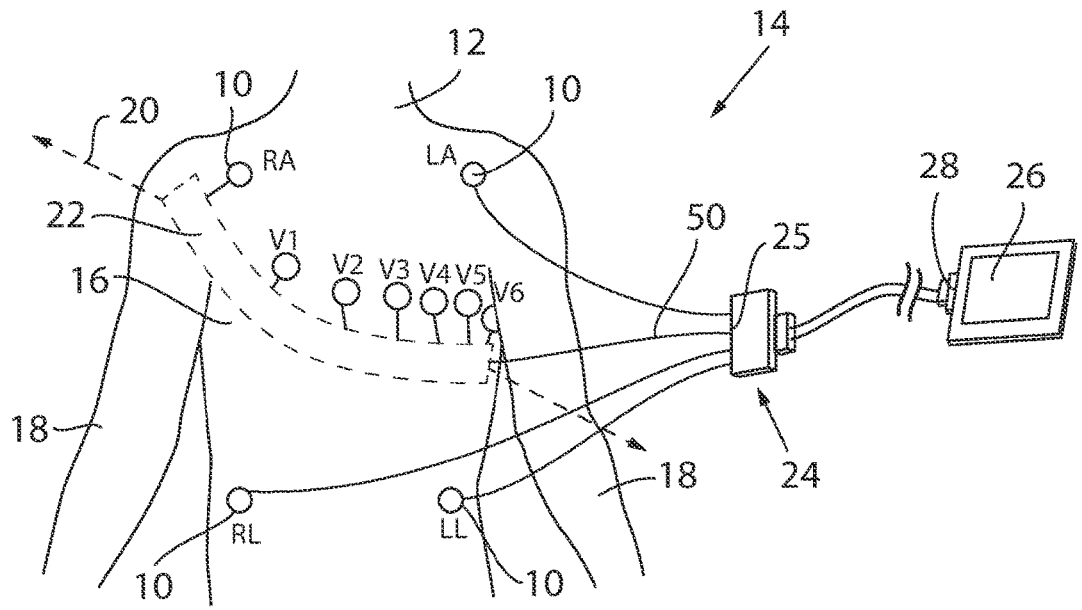
FIG. 1 is a schematic diagram of an lead array of the present invention positioned on a patient's chest and connecting the RA lead and V1-V6 leads to a coaxial cable attachable to a trunk cable communicating with an ECG monitor, the trunk cable also connecting the LA lead, LL lead, and RL lead to the ECG monitor.

Referring now to FIG. 1, an electrocardiogram (ECG) is conducted by placing conductive pads or surface electrodes 10 on the skin of a patient 12. The electrodes 10 are comprised generally of an electrode conducting paste or gel receiving the ionic currents in the body and metal electrode transmitting the electrical current to a connectable lead. The electrode 10 commonly takes the form of a flat paper-thin sticker or a self-adhesive circular pad. The electrodes 10 detect small electrical changes that are a consequence of cardiac muscle depolarization followed by repolarization during each cardiac cycle or heartbeat as understood in the art.

Specifically, in one embodiment, the electrodes 10 employ a thin base layer of compliant material which supports a metal electrode, for example, in the form of a male metallic snap fastener element. The base layer also supports a pad filled with conductive paste or gel in intimate contact with the base of the snap fastener element. The base of the snap fastener element may be coated with silver and when it comes into contact with the conductive paste or gel, may form a silver/silver chloride coating enhancing conductive properties. The underside of the base layer is coated with a suitable adhesive and when the base layer is adhered to the patient's skin, the gel pad is pressed against the skin with the conductive gel making good electrical contact between the skin and the snap fastener element. Electrical connection to a lead is made by attaching the snap fastener element to a mating fastener element of the lead. An electrode 10 which may be used with the present invention is as described in U.S. Pat. Nos. 3,828,766 and 3,977,392, both of which are hereby incorporated by reference. In an alternative embodiment of the invention, the electrodes 10 may be textile electrodes made of conductive yarns by weaving, knitting or embroidering processes or by coating or printing conductive polymers on non-conductive fabrics.

For a 12-lead ECG, the ECG assembly 14 includes ten electrodes 10 placed on the patient's chest 16 and limbs 18. The ten electrodes 10 of a 12-lead ECG include placements: (1) on the right arm, "RA", (2) on the left arm, at a same location as the right arm, "LA", (3) on the right leg at the lower end of the inner aspect of the calf muscle, "RL", (4) on the left leg, at a same location as the right leg, "LL", (5) in the fourth intercostal space just to the right of the sternum, "V1", (6) in the fourth intercoastal space just to the left of the sternum, "V2", (7) between leads V2 and V4, "V3", (8) in the fifth intercostal space in the mid-clavicular line, "V4", (9) horizontally even with V4, in the left interior axillary line, "V5", and (10) horizontally even with V4 and V5 in the midaxillary line, "V6". The two arm electrodes, "RA" and "LA", and two leg electrodes, "RL", "LL", define the limb leads while the six chest electrodes, V1-V6, define the precordial leads. Any pair of electrodes 10 can measure the electrical potential difference between two corresponding locations of attachment, each pair forming a "lead."

The six chest electrodes, V1-V6, can be placed along a transverse axis 20 extending obliquely across the patient's chest 16 in a generally downward direction from a right shoulder of the patient's body to a left side of the patient's chest. The RA electrode is generally positioned along the transverse axis 20 thus facilitating the connection of the RA electrode and the V1-V6 electrodes to a single lead array 22 as described with respect to the present invention. In some embodiments, the RA electrode may be omitted from the lead array 22. In one embodiment of the present invention, the RL electrode may also be included with the lead array 22 as it also generally lies along the axis 20.

The RA electrode and the V1-V6 electrodes 10 may be electrically connected to individually insulated electrical wires 34, normally copper or aluminum wires coated with rubber or plastic insulation, which are further connected to an ECG trunk cable 24 which is able to support multiple connectors at a first input end 25, including the electrical wires 34 from the RA electrode and the V1-V6 electrodes, and an ECG monitor 26 at a second output end 28 for visualization of the ECG signals. The LA electrode, RL electrode, and LL electrode, respectively, may also be electrically connected to the first input end 25 of the ECG trunk cable 24 to provide respective signals to the ECG monitor 26 for visualization of the ECG signals.

Figure 2:
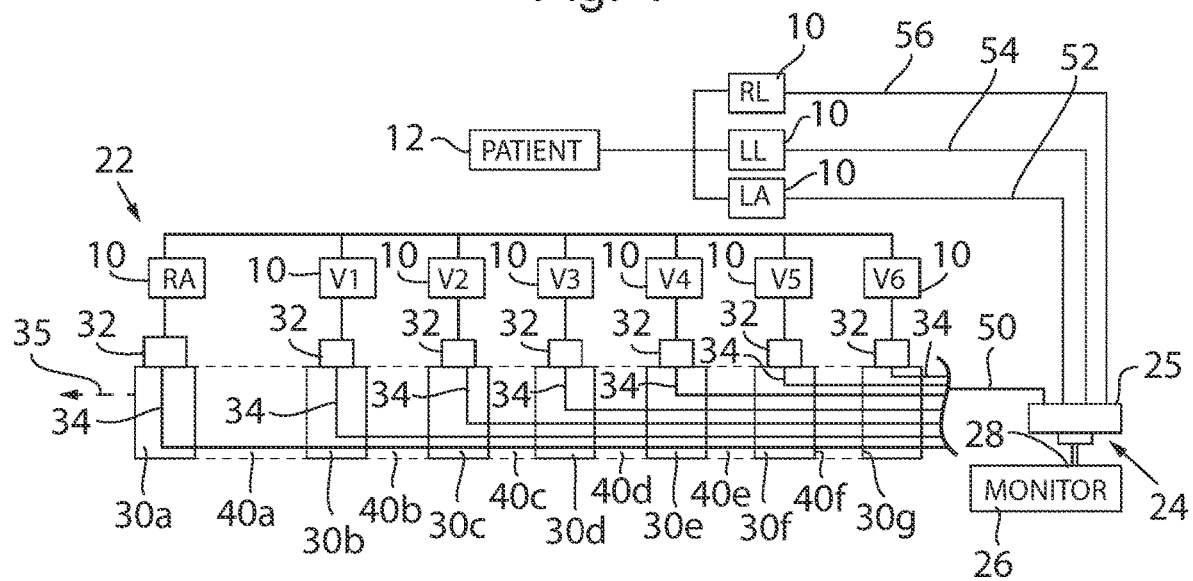
FIG. 2 is a block diagram of the lead array of FIG. 1 supporting seven electrode connectors, each connected to the RA lead and V1-V6 leads, respectively, and each electrode connector is interconnected by at least one electrical connector running along the lead array.

Referring to FIG. 2, the lead array 22 may incorporate a number of electrode connectors 30a-g extending along an array axis 35, defined by the lateral extent of the outermost electrode connectors 30a-g and in which the axis 35 may be curved, the electrode connectors 30a-g configured for electrical attachment via electrical fasteners 32 to the RA electrode and the V1-V6 electrodes on the body of the patient 12. A first electrode connector 30a may be attachable to the RA electrode, a second electrode connector 30b may be attachable to the V1 electrode, a third electrode connector 30c may be attachable to the V2 electrode, a fourth electrode connector 30d may be attachable to the V3 electrode, a fifth electrode connector 30e may be attachable to the V4 electrode, a sixth electrode connector 30f may be attachable to the V5 electrode, and a seventh electrode connector 30g may be attachable to the V6 electrode.

Each of the electrode connectors 30a-g may include an electrical fastener 32 for electrically coupling the electrode 10 to the electrical wire 34. The electrical fastener 32 may be a snap, pinch, clip or alligator clip type attachment mechanism that can attach to both snap and tab style electrodes 10. The electrical fastener 32 may extend outwardly from the electrode connector 30a-g. In one embodiment of the present invention, the electrical fastener 32 may be attached to the electrode connector 30a-g, for example welded to the electrode connector 30a-g, whereas in an alternative embodiment, the electrical fastener 32 may extend outwardly from the electrode connector 30a-g, for example by an electrical wire, the electrode connector 30a-g displaced slightly from the electrode 10. In this respect, the electrode connector 30a-g does not need to be placed directly on the electrode 10 but can be spaced slightly away from the electrode 10 while still being connected via the outwardly extended electrical fastener 32 and/or electrical wire. The electrical wire may be at least less than two inches in length or at least less than one inch in length or may be less than the inter-electrode spacing.

Each of the electrode connectors 30a-g may be labeled on an outer surface using a graphic or text label (not shown) clearly denoting the desired corresponding connection of each of the electrode connectors 30a-g to the respective electrode 10. For example, the first electrode connector 30a may include a "RA" label denoting the connection of the first electrode connector 30a to the RA electrode, the second electrode connector 30b may include a "V1" label denoting the connection of the second electrode connector 30b to the V1 electrode, and so forth.

The electrical fastener 32 is connected to the electrical wire 34 that runs through the electrode connector 30a-g along the array axis 35 to be further physically interconnected with the other electrode connectors 30a-g but electrically separate from the other electrode connectors 30a-g. Each of the electrode connectors 30a-g may be interconnected in succession to an adjacent electrode connector by cable corrals 40a-f, the cable corrals 40a-f being separate from the insulation of the individual electrical wires 34, and extending therebetween each of the electrode connectors 30a-g also along the array axis 35.

For example, a first cable corral 40a may connect or be positioned between the first electrode connector 30a and the second electrode connector 30b, a second cable corral 40b may connect or be positioned between the second electrode connector 30b and the third electrode connector 30c, a third cable corral 40c may connect or be positioned between the third electrode connector 30c and the fourth electrode connector 30d, a fourth cable corral 40d may connect or be positioned between the fourth electrode connector 30d and the fifth electrode connector 30e, a fifth cable corral 40e may connect or be positioned between the fifth electrode connector 30e and the sixth electrode connector 30f, and a sixth cable corral 40f may connect or be positioned between the sixth electrode connector 30f and the seventh electrode connector 30g. In this respect, the electrode connectors 30a-g and cable corrals 40a-f may form a continuous alternating chain of electrode connectors 30a-g and cable corrals 40a-f.

The cable corrals 40a-f provide for the shortening and lengthening of a distance between respective electrode connectors 30a-g so that each of the electrode connectors 30a-g may be attached to each of the RA electrode and the V1-V6 electrodes, respectively, in a manner that accommodates spatial distances between the RA electrode and the V1-V6 electrodes. For example, a longer distance may be provided between the first electrode connector 30a and the second electrode connector 30b accommodating for the longer distance between the RA electrode and V1 electrode, whereas a shorter distance may be provided between the sixth electrode connector 30f and seventh electrode connector 30g accommodating for a shorter distance between the V5 electrode and V6 electrode. The shortening or lengthening of the distance between respective electrode connectors 30a-g may also accommodate different body sizes of patients 12 and differences in size between adults, children, and infant patients. For example, a longer distance may be provided between electrode connectors 30a-g for adults than for children. The cable corrals 40a-f are also flexible to allow for spatial repositioning of the electrode connectors 30a-g. For example, adapting for protrusions on the patient's chest.

The electrical wire 34, connected to the electrical fastener 32 of each electrode connector 30a-g, may extend outwardly from the electrode connector 30a-g and run through the cable corrals 40a-f along the array axis 35 between electrode connectors 30a-g in a manner which accumulates and consolidates the electrical wire 34 as they run along each of the electrode connectors 30a-g along the array axis 35 of the lead array 22. In this respect, the electrical wire 34 is physically connected to each of the electrode connectors 30a-g as it runs along the array axis 35 of the lead array 22.

For example, the first electrical wire 34a of the first electrode connector 30a may pass through the first cable corral 40a, through the second electrode connector 30b, through the second cable corral 40b, through the third electrode connector 30c, through the third cable corral 40c, through the fourth electrode connector 30d, the fourth cable corral 40d, through the fifth electrode connector 30e, through the fifth cable corral 40e, through the sixth electrode connector 30f, through the sixth cable corral 40f, and through the seventh electrode connector 30g. The first electrical wire 34a is joined by the second electrical wire 34b of the second electrode connector 30b which passes through the second cable corral 40b, through the third electrode connector 30c, through the third cable corral 40c, through the fourth electrode connector 30d, the fourth cable corral 40d, through the fifth electrode connector 30e, through the fifth cable corral 40e, through the sixth cable corral 40f, and through the seventh electrode connector 30g. This pattern is repeated in a similar manner for the third electrical wire 34c, fourth electrical wire 34d of the fourth electrode connector 30d, the fifth electrical wire 34e of the fifth electrode connector 30e, the sixth electrical wire 34f of the sixth electrode connector 30f, and the seventh electrical wire 34g of the seventh electrode connector 30g. In this respect, each of the first electrical wire 34a, second electrical wire 34b, third electrical wire 34c, fourth electrical wire 34d, fifth electrical wire 34e, sixth electrical wire 34f, and seventh electrical wire 34g accumulate to extend outwardly from the final seventh electrode connector 30g. The first electrical wire 34a of the first electrode connector 30a (the first electrode connector in the chain) thus interconnects each of the electrode connectors 30a-g and each of the cable corrals 40a-f along the chain of the lead array 22.

The seven electrical wires 34a-34f of each of the seven electrode connectors 30a-30f may be a single cable 50 extending along the array axis 35, for example, a coaxial shielded cable allowing for the multiple wires to be physically connected in an insulated outer sheath, but each individual electrical wires 34 separated insulated and electrically separate, or a ribbon cable allowing for the wires to be physically connected to each other on a common flat plane, but each individual electrical wires 34 separated insulated and electrically separate, as further discussed below, which may then be connected to an input end 25 of a trunk cable 24.

In one embodiment, the electrical wires 34 are physically connected by an integrated, insulated sheath such as a ribbon cable allowing the conducting electrical wires 34 to run parallel on a common flat plane but are electrically separate to deliver different electrical signals. The individual electrical wires 34 may be coated with a silicone rubber and molded together onto a single cable. Other materials used to insulate the electrical wires 34 from each other and the environment are Teflon, olefin materials, and polyvinyl chloride (PVC). Each of the individual electrical wires 34 may take a different color to help distinguish each electrical wire 34.

The trunk cable 24 receives, along the array axis 35, the single cable 50 from the RA electrode and V1-V6 electrodes, as well as receives an electrical wire 52 from the LA electrode, an electrical wire 54 from the LL electrode, and an electrical wire 56 from the RL electrode. Different trunk cables 24 may omit some electrode connections, such as the RA electrode, or may vary in their inputs to allow for different combinations of electrode connections.

The trunk cable 24 may include labels (not shown) clearly denoting the desired corresponding connection of the coaxial cable 50, the electrical wire 52, the electrical wire 54, or the electrical wire 56. For example, the trunk cable 24 may include a "COAX" label denoting the connection of the single cable 50 to the proper input of the trunk cable 24 or a "LA" label denoting the connection of the electrical wire 52 to the proper input of the trunk cable 24 and so forth.

An output end 28 of the trunk cable 24 is further connected to the ECG monitor 26 to provide electrical signals to the ECG monitor 26 as understood in the art.

First Embodiment

Figure 3:
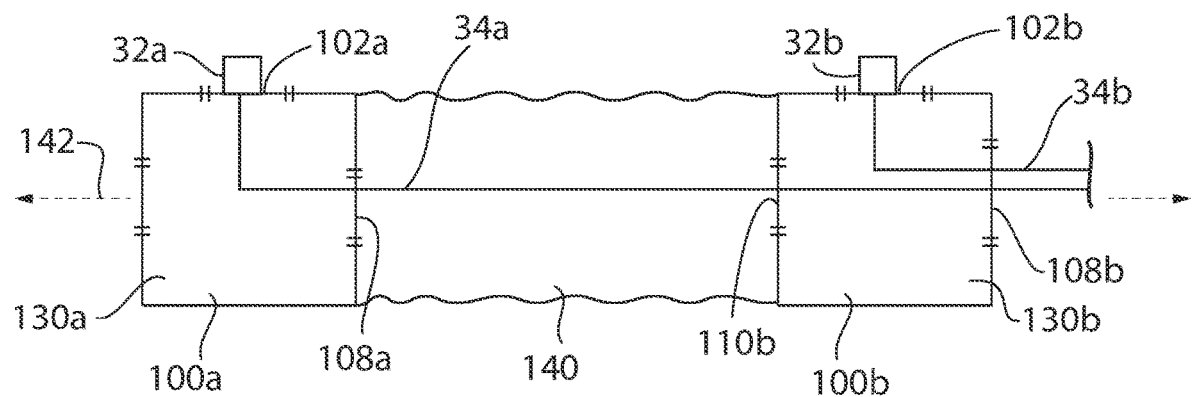
FIG. 3 is a schematic representation of a first embodiment of the present invention showing two electrode connectors of the lead array of the present invention being connected by an expandable cord corral and shown in an expanded state with the electrical connector extending through the cord corral.
Figure 4:
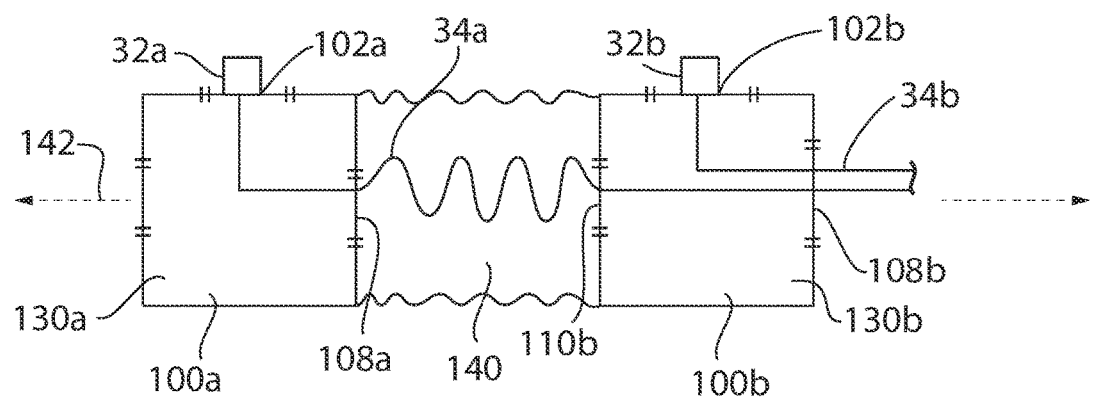
FIG. 4 is a schematic representation of the embodiment of FIG. 3 shown in a collapsed state with the electrical connector bunched together within the cord corral.

Referring to FIGS. 3 and 4, in a first embodiment of the present invention, the electrode connectors 30a-g, which are generally described above with respect to FIG. 2, comprise specifically of electrical hubs 130a and 130b defined by a rectangular housing 100a-b holding the electrical fasteners 32 and electrical wires 34. The housing 100a-b may include a lead port allowing the electrical fasteners 32 to extend to the electrodes 10 on the patient 12 and an inlet port and outlet port to allow the electrical wires 34 to extend through the housing 100a-b and connect to the electrical fasteners 32. The first electrode connector 30a in the series may not require an inlet port since there is no adjacent electrode connector which require electrical wires 34 to enter.

In the exemplary illustration of FIGS. 3 and 4, the first electrical hub 130a (left) and the second electrical hub 130b (right) are shown. With specific reference to the first electrical hub 130a, the housing 100a may have a lead port 102a allowing for the extension of the electrical fastener 32a outwardly from the housing 100a. In one embodiment, the electrical fastener 32a may be a Sure-Lock electrode clip, manufactured by GE Healthcare, having a locking metal clip, or an alligator clip supported by the housing 100a and extending upwardly through the lead port 102a of the rectangular housing 100a to be connectable to the electrodes 10 on the patient 12, as illustrated in FIGS. 1 and 2.

The first electrical fastener 32a is attached to a first electrical wire 34a extending through the housing 100a of the first electrical hub 130a and outwardly through an outlet port 108b, generally displaced 90-degrees from the lead port 102a. The first electrical wire 34a egresses the first electrical hub 130a through the outlet port 108a and extends through the cable corral 40a connecting the first electrical hub 130a with the neighboring second electrical hub 130b. The first electrical wire 34a then enters the inlet port 110b of the neighboring second electrical hub 130b and runs through the housing 100b of the second electrical hub 130b to the outlet port 108b of the second electrical hub 130b, and so forth.

In a similar manner, with specific reference to the second electrical hub 130b, the second electrical wire 34b of the second electrical hub 130b extends from the electrical fastener 32b and runs through the housing 100b of the second electrical hub 130b to join the first electrical wire 34a and egress the second electrical hub 130b through the outlet port 108b to coextensively extend along the lead array 22 with the first electrical wire 34a, in a direction generally running from a right side of the patient's body (patient's right shoulder) to the left side of the patient's body (left side of the patient's chest).

In the first embodiment of the present invention, the cable corrals 40a-f may be flexible bellows or expansion joints 140 that may be collapsed or expanded to vary the distance between adjacent electrical hubs 130a-b. The expansion joints 140 may be corrugated tubes comprised of stacked "rings" formed of alternating ridges and grooves, resembling the flexible part of a straw, that can fold onto each other to collapse along a longitudinal axis 142 in a compressed state (FIG. 4) and may be pulled apart in an expanded state (FIG. 3) along the longitudinal axis 142. In this respect, the movement of the expansion joints 140 is compressive, where the expansion joints 140 shorten in length, or extensive where the expansion joints 140 extend in length. The expansion joints 140 are also flexible and are capable of being bent without collapsing the internal passageway to allow for the positioning of adjacent electrical hubs 130 to be adjusted in three dimensions. In this respect, movement perpendicular to the longitudinal axis 142 is a shearing movement with one end offset from the other, usually with the ends of the expansion joints 140 remaining parallel to each other.

When each of the cable corrals 40 of the lead array 22 are in a fully expanded state, the lead array 22 is at its greatest length. In this state, the first electrical wire 34a may be nearly taut, thus representing the greatest length of electrical wire 34a needed to extend along the lead array 22. Similarly, the second electrical wire 34b of the second electrical hub 130b is nearly taut when each of the expansion joints 140, except for the first cable corral 40a, are in a fully expanded state, and so forth for the remaining electrical wires 34. Thus, the length of the electrical wires 34 needed is a distance between its corresponding electrode connector 30 and a length of the lead array 22 the electrical wire 34 runs through when the cable corrals 40 are fully extended.

When one or more of the cable corrals 40a-f are in a compressed state, the electrical wire 34 is bunched or gathered within the expansion joints 140. The expansion joints 140 provides an inner lumen allowing for the electrical wires 34 to bunch. A shortest length of the lead array 22 is represented by the complete compression of each of the cable corrals 40a-f of the lead array 22.

Other types of compressible or collapsible cable corrals 40a-f are contemplated, such as telescoping tubes, that allow for the lengthening and shortening of the cable corrals 40a-f, and other compressible tube constructions.

Although only the first electrical hub 130a and second electrical hub 130b are shown in FIGS. 3 and 4, it is understood that the subsequent connection of the remaining electrode connectors 30a-g and cable corrals 40a-f is made in a similar manner.

Second Embodiment

Figure 5:
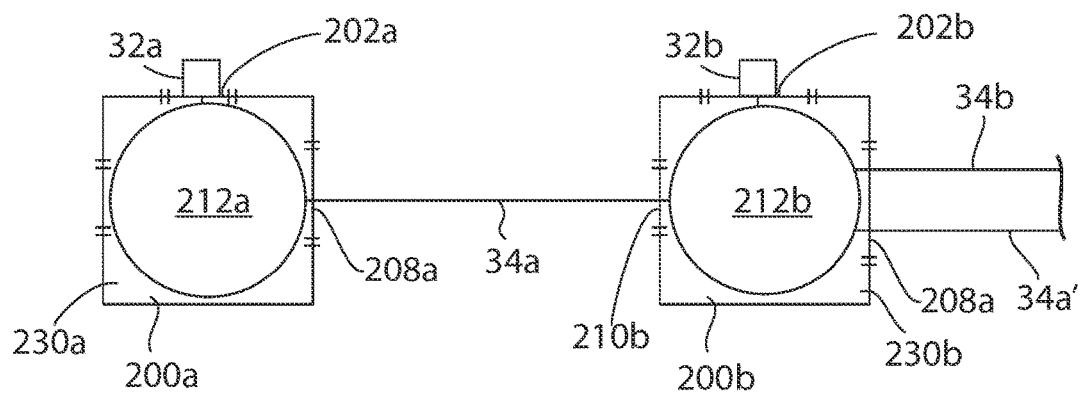
FIG. 5 is a schematic representation of a second embodiment of the present invention showing two electrode connectors of the lead array of the present invention being connected by an electrical connector that is retractable and expandable by winding and unwinding on a spool assembly.
Figure 6:
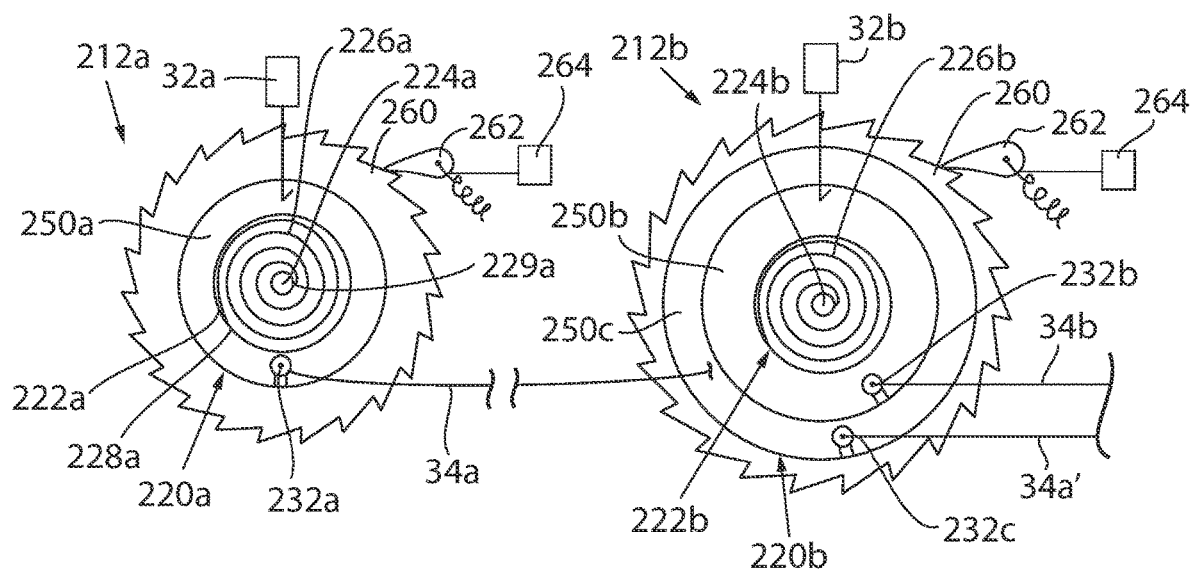
FIG. 6 is a schematic representation of the embodiment if FIG. 5 showing the spool assembly of two electrode connectors each having a spool and at least one slip ring providing an electrical connection between the rotating slip ring and a stationary electrical contact.

Referring to FIGS. 5 and 6, in a second embodiment of the present invention, the electrode connectors 30a-g, which are generally described above with respect to FIG. 2, are spool hubs 230a, 230b defined by a spool housing 200 holding a spool assembly 212a-b. The spool housing 200 may include a lead port allowing the electrical fasteners 32 to extend to the electrodes 10 on the patient 12 and an inlet port and outlet port to allow the electrical wires 34 to extend through the spool housing 200 and connect to the electrical fasteners 32. The first electrode connector 30a in the series may not require an inlet port since there is no adjacent electrode connector which require electrical wires 34 to enter.

In the exemplary illustration of FIGS. 5 and 6, the first spool hub 230a (left) and second electrical hub 230b (right) are shown. With specific reference to the first spool hub 230a, the spool housing 200a may have a lead opening 202a allowing for the outwardly extension of the electrical fastener 32a from the spool housing 200a. In one example, the electrical fastener 32a may be a sure-lock electrode clip having a locking metal clip or an alligator clip supported by the spool housing 200a and extending upwardly through the lead port 202a of the spool housing 200a to be connectable to the electrodes 10 on the patient 12 as previously illustrated in FIGS. 1 and 2.

The electrical fastener 32a of the first spool hub 230a may electrically communicate with a spool assembly 212a of the first spool hub 230a. The spool assembly 212a may further communicate an electrical signal from the electrical fastener 32a to a first electrical wire 34a wound around the spool assembly 212a. The first electrical wire 34a may extend from the spool assembly 212a and egress through an outlet port 208a of the spool housing 200a, which, in one embodiment, is displaced 90 degrees from the lead opening 202a.

With specific reference to the second spool hub 230b, the first electrical wire 34a egresses the outlet port 208a and extends into the inlet port 210b of the spool housing 200b where it communicates with a spool assembly 212b of the spool housing 200b. The spool assembly 212b may further communicate an electrical signal from the electrical fastener 32a to a first electrical wire 34a' wound around the spool assembly 212b. The first electrical wire 34a' may extend from the spool assembly 212b and egress through an outlet port 208b of the spool housing 200b.

In a similar manner, the electrical fastener 32b of the second spool hub 230b electrically communicates with the spool assembly 212b of the second spool hub 230b. The spool assembly 212b may further communicate an electrical signal from the electrical fastener 32b to a second electrical wire 34b wound around the spool assembly 212b. The second electrical wire 34b then extends from the spool assembly 212b and exits through the outlet port 208, which, in one embodiment, is displaced 90 degrees from the lead opening 202.

The second electrical wire 34b and first electrical wire 34a' may extend from the spool assembly 212b and egress through an outlet port 208b of the spool housing 200b coextensively along the lead array 22 in a general direction from a right side of the patient's body (patient's right shoulder) to the left side of the patient's body (left side of the patient's chest).

Referring now specifically to FIG. 6, the cable corrals 40a-f may be spool assemblies 212a-b used to retract and extend the first and second electrical wires 34a, 34b by winding and unwinding the wires from a spool and thereby varying a length of the first electrical wire 34a extending between the first and second spool hubs 230a, 230b, and a length of the first electrical wire 34a' and second electrical wire 34b extending between the second spool hub 230b and third spool hub (not shown). Thereby, the spool assemblies 212a-b are able to vary the distance between adjacent spool hubs 230.

With specific reference to the first spool assembly 212a, the spool assembly 212a may include a reel 220a on which the first electrical wire 34a is wound therearound and having a central hole 222a which receives an axle 224a of the housing 200a on which the reel 220a rotates.

A constant force spring or spiral steel spring 226a may be provided between the reel 220a and the housing 200a for providing a reeling force to the reel 220a during retraction of the first electrical wire 34a. The spiral spring 226a has an outer end 228a that is anchored to the reel 220a and an inner end 229a anchored to the axle 224a. The axle 224a may be provided with a slot for anchoring the inner end 229a of the spiral spring 226a. The central hole 222a of the reel 220a is placed on the axle 224a to allow the reel 220a to rotate which compresses the spiral spring 226a to store kinetic energy which biases the reel 220a to retract the first electrical wire 34a.

An electrically conductive slip ring 250a is mounted onto the reel 220a and is configured to rub against stationary wire contacts of the electrical fastener 32a to transmit the electrical signals from the electrical fastener 32a through the rotating slip ring 250a to the connected first electrical wire 34a. An inner end of the first electrical wire 34a is mechanically attached to the reel 220a to be wound therearound and is electrically attached to a solder point 232a on the slip ring 250a, the slip ring 250a having a circular pattern coaxial to the axle 224a forming a continuous electrode. The first electrical wire 34a carries the electrical signal away from the reel 220a.

In a similar manner, the second spool assembly 212b may include a reel 220b on which the second electrical wire 34b is wound around and having a central hole 222b which receives an axle 224b of the housing 200b on which the reel 220b rotates.

A constant force spring or spiral spring 226b is provided between the reel 220b and the housing 200b as similarly described above with respect to the first spool assembly 212a.

An electrically conductive slip ring 250b is mounted to the reel 220b and is configured to rub against stationary wire contacts of the electrical fastener 32b to transmit the electrical signals from the electrical fastener 32b through the rotating slip ring 250b to the connected second electrical wire 34b. An inner end of the second electrical wire 34b is mechanically attached to the reel 220b to be wound therearound and electrically attached to a solder point 232b on the slip ring 250b, the slip ring 250b having a circular pattern coaxial to the axle 224b forming a continuous electrode.

In addition to the electrically conductive slip ring 250b mounted to the reel 220b, a subsequent electrically conductive slip ring 250c is mounted to the reel 220b and is configured to rub against stationary wire contacts of the first electrical wire 34a to transmit the electrical signals from the first electrical wire 34a through the rotating slip ring 250c to a first electrical wire 34a' extending outwardly from the reel 220b. An inner end of the first electrical wire 34a' is mechanically attached to the reel 220b to be wound therearound and is electrically attached to a solder point 232c on the slip ring 250c, the slip ring 250c having a circular pattern coaxial to the axle 224a forming a continuous electrode.

The second electrical wire 34b carries a first electrical signal away from the reel 220b, and the first electrical wire 34a' carries a second electrical signal away from the reel 220b. It is understood that a subsequent electrically conductive slip ring 250a-c is added to the reel 220 for each additional electrical wire 34 extending along the lead array 22 so that each electrical wire 34 sends a separate and distinct electrical signal to the trunk cable 24.

In one embodiment of the present invention, the spool assembly 212 may include a ratchet mechanism having a plurality of angled ratchet teeth 260 mounted on an outer edge of the flange of the reel 220. A spring-loaded finger or pawl 262 is engaged with the teeth 260 to allow rotation of the reel 220 in a first direction but stops the reel 220 from rotation in an opposite direction. When a release button 264 is actuated, the spring-loaded pawl 262 is moved away from engagement from the teeth 260. Thus, the spool assembly 212 enables the extension and retraction of the first and second electrical wire 34a, 34b to a desirable length and locks the reel 220 in position once the first and second electrical wire 34a, 34b have reached the desirable length. The ratchet mechanism also enables the automatic retraction of the first and second electrical wire 34a, 34b when the release button 264 is actuated via the spiral spring 226a-b described above.

Other variations of spool assemblies 212a-b is contemplated that allow for the lengthening and shortening of the cable corrals 40a-f by winding of the electrical wires 34 onto the reel 220 of the spool assemblies 212a-b.

Although only the first spool hub 230a and second spool hub 230b are shown in FIGS. 5 and 6, it is understood that the subsequent connection of the remaining electrode connectors 30a-g and cable corrals 40a-f is made in a similar manner.

Third Embodiment

Figure 7:
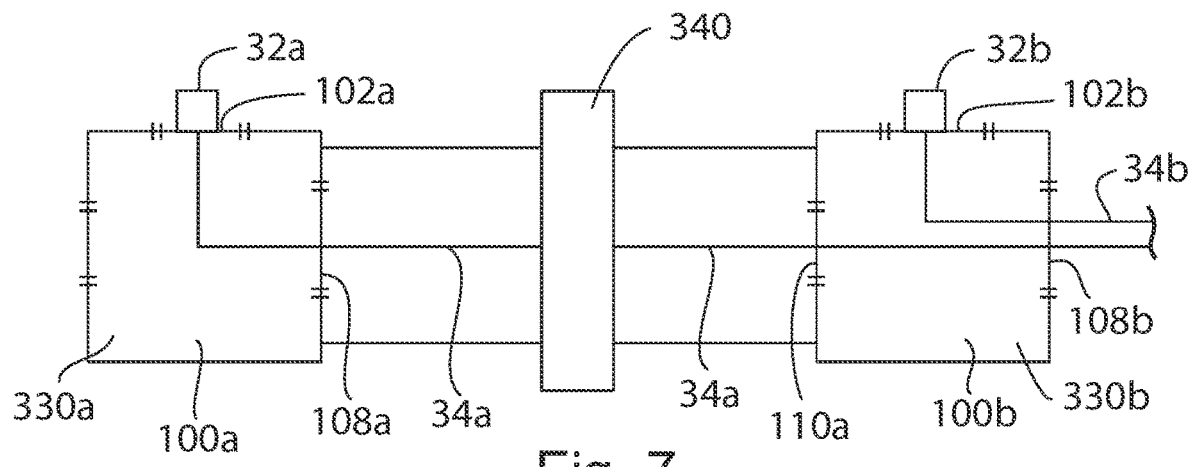
FIG. 7 is a schematic representation of a third embodiment of the present invention showing two electrode connectors of the lead array of the present invention being connected by an electrical connector that is retractable and expandable by a cable shortener.
Figure 8:
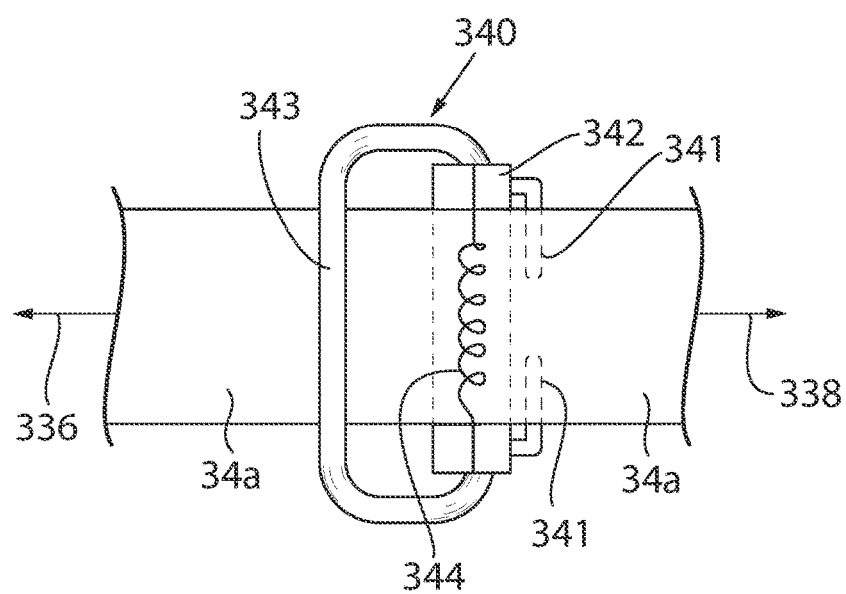
FIG. 8 is a schematic representation of the embodiment if FIG. 7 showing a seat belt retractor providing a spool for winding of the electrical connector thereon.

Referring to FIGS. 7 and 8, in a third embodiment of the present invention, the electrode connectors 30a-g, which are generally described above with respect to FIG. 2, are electrical hubs 330a and 330b defined by the rectangular housing 100a-b holding the electrical fasteners 32 and electrical wires 34 as described with respect to the first embodiment of FIGS. 3 and 4.

In the third embodiment of the present invention, the cable corrals 40a-f may be winders 340 allowing for the coiling of the first electrical wire 34a between the electrical hubs 330a and 330b. The first electrical wire 34a may be wide and flat electrical wires such as a ribbon wire that are able to be wound around the winders 340 of this third embodiment.

As shown in FIG. 8, the winders 340 may be seat belt retractor type devices, for example as manufactured by Chevrolet, which allow a midsection of the electrical wires 34 to maintain a fixed connection under tabs 341 of a spool 342 while the electrical wires 34 are wound around the spool 342. A hinge 343 maintains one end of the electrical wire 34 above the spool 342 in a first direction 336 while the other end of the electrical wire 34 remains below the spool 342 in a second opposite direction 338 as it is wound around the spool 342, to shorten and lengthen the length of electrical wire 34a. A spring 344 inside the spool 342 retains the spring-loaded spool 342 in a retracted position so that the electrical wire 34 may be extended from the spool 342 and automatically retracted back onto the spool 342.

The winders 340 may alternatively take the form of a spool (not shown), for example, the spool described in U.S. Pat. No. 7,108,216, and hereby incorporated by reference, which describes a two-sided spool for winding and unwinding a length of flat electrical wire. The spool has an outer surface associated with an expansion chamber within the housing portion, an inner channel configured to hold a wound length of flat electrical cable and a passage extending between the outer surface and the inner channel. A flat electrical cable has a first portion disposed in the expansion chamber, a second portion disposed in the inner channel, and a third portion disposed in the passage to follow a path from the outer surface of the spool to the inner channel.

Method of Operation

In operation, the lead array 22 may be placed onto the patient's chest after the electrodes 10 have been placed on the patient 12. The electrodes 10 may be placed at the appropriate positions on the patient 12 as understood in the art.

In one embodiment of the present invention the electrode connectors 30a-g of the lead array 22 may be aligned with the electrodes 10 starting with a position closest to the trunk cable 24 and ECG monitor 26, for example, starting with aligning the V6 electrode and moving outward toward the RA electrode.

First, the seventh electrode connector 30g is positioned below the V6 electrode and the electrical fastener 32 of the seventh electrode connector 30g is clipped or otherwise attached to the V6 electrode.

The sixth electrode connector 30f is then extended to a position below the V5 electrode by extending the sixth cable corral 40f away from the seventh electrode connector 30g. The electrical fastener 32 of the sixth electrode connector 30f is clipped or otherwise attached to the V5 electrode.

The fifth electrode connector 30e is then extended to a position below the V4 electrode by extending the fifth cable corral 40e away from the sixth electrode connector 30f. The electrical fastener 32 of the fifth electrode connector 30e is clipped or otherwise attached to the V4 electrode.

The fourth electrode connector 30d is then extended to a position below the V3 electrode by extending the fourth cable corral 40d away from the fifth electrode connector 30e. The electrical fastener 32 of the fourth electrode connector 30d is clipped or otherwise attached to the V3 electrode.

The third electrode connector 30c is then extended to a position below the V2 electrode by extending the third cable corral 40c away from the fourth electrode connector 30d. The electrical fastener 32 of the third electrode connector 30c is clipped or otherwise attached to the V2 electrode.

The second electrode connector 30b is then extended to a position below the V1 electrode by extending the second cable corral 40b away from the third electrode connector 30c. The electrical fastener 32 of the second electrode connector 30b is clipped or otherwise attached to the V1 electrode.

Lastly, the first electrode connector 30a is then extended to a position below the RA electrode by extending the first cable corral 40a away from the first electrode connector 30b. The electrical fastener 32 of the first electrode connector 30a is clipped or otherwise attached to the RA electrode.

The single cable 50 carrying the seven electrical wires 34a-34f of each of the seven electrode connectors 30a-30f is then connected to the input end 25 of the trunk cable 24. The output end 28 of the trunk cable 24 is connected to the ECG monitor 26 for visualization of the electrical signals from each of the electrodes 10, respectively, as understood in the art.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference, which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context. When elements are indicated to be electrically connected, that connection may be direct or through an intervening conductive element.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

To aid the Patent Office and any readers of any patent issued on this application in interpreting the claims appended hereto, applicants wish to note that they do not intend any of the appended claims or claim elements to invoke 35 U.S.C. 112(f) unless the words "means for" or "step for" are explicitly used in the particular claim.

The invention claimed is:

1. A wire harness for connecting surface electrodes on a patient to ECG monitoring equipment, the harness comprising:
   a set of fasteners each releasably attachable to a respective surface electrode of a set of surface electrodes for electrical communication therewith, wherein each of the set of fasteners are supported by a respective housing of a set of housings;
   a set of wires each connected at distal ends to a corresponding one of the set of fasteners, with each individual wire separately connecting a fastener to the ECG monitoring equipment;
   a set of cable corrals each positioned between a pair of the set of housings, with a proximal-most cable corral receiving the entire set of wires and each given cable corral distal to the proximal-most cable corral receiving one fewer of the set of wires than a cable corral proximally-preceding the given cable corral, the cable corrals operating to collect excess wire when a separation in distance between fasteners is reduced; and
   wherein shortening or lengthening of a respective cable corral of the set of cable corrals between two adjacent housings of the set of housings changes based upon a shortened or lengthened distance between the set of fasteners supported by the two adjacent housings of the set of housings and based upon a shortened or lengthened distance between adjacent surface electrodes of the set of surface electrodes.

2. The wire harness of claim 1 further comprising a plurality of surface electrodes having a snap element connectable to the set of fasteners and a pad contacting the patient's skin.

3. The wire harness of claim 1 wherein the set of fasteners are physically interconnected.

4. The wire harness of claim 3 wherein the set of cable corrals is an integrated insulated sheath.

5. The wire harness of claim 1 wherein the set of cable corrals are expandable sleeves configured for corralling the set of wires therein therein.

6. The wire harness of claim 5 wherein the expandable sleeves are expandable and compressible along a longitudinal axis of expandable sleeves and moveable perpendicular to the longitudinal axis with the ends of the expandable sleeves offset from each other.

7. The wire harness of claim 1 wherein the set of electrode connectors includes at least seven electrode connectors connected to a RA electrode and V1-V6 electrodes, respectively.

8. The wire harness of claim 1 wherein the set of fasteners comprise a clip connectable to an ECG electrode on the patient.

9. The wire harness of claim 8 wherein the clip is an alligator clip.

10. The wire harness of claim 1 wherein at least one wire of the set of wires are connectable to a trunk cable along an input axis of the trunk cable.

11. A wire harness for connecting surface electrodes on a patient to ECG monitoring equipment, the harness comprising: a set of fasteners each releasably attachable to a respective surface electrode of a set of electrodes for electrical communication therewith, wherein each of the set of fasteners are supported by a respective housing of a set of housings;
  a set of wires each connected at distal ends to a corresponding one of the set of fasteners, with each individual wire separately connecting a fastener to the ECG monitoring equipment;
  a set of cable corrals each positioned within a respective housing of the set of housings, with a proximal-most cable corral receiving the entire set of wires and each given cable corral distal to the proximal-most cable corral receiving one fewer of the set of wires than a cable corral proximally-preceding the given cable corral, the cable corrals operating to collect excess wire when a separation in distance between fasteners is reduced;
  wherein a shortening or lengthening of a distance between two adjacent cable corrals of the set of cable corrals in the set of housings changes based upon a shortened or lengthened distance between the set of fasteners supported by the set of housings that the two adjacent cable corrals are positioned within, and based upon a shortened or lengthened distance between adjacent surface electrodes of the set of surface electrodes, and wherein the set of cable corrals are rotatable spools of the set of wires around the spools.

12. The wire harness of claim 11 wherein the rotating spool has a slip ring wherein a stationary electrical contact from an electrode of the patient electrically communicates with the rotatable slip ring.

13. The wire harness of claim 12 wherein the at least one wire of the set of wires is mechanically attached to the spool and electrically connected to the slip ring.

14. The wire harness of claim 11 wherein the spools further include a constant force spring.

15. The wire harness of claim 14 wherein the spools include a rim of teeth interacting with a spring-loaded finger that engages with the teeth.

16. A method of connecting surface electrodes on a patient to ECG monitoring equipment using a harness having:
  a set of fasteners each releasably attachable to a respective surface electrode of a set of surface electrodes for electrical communication therewith, wherein each of the set of fasteners are supported by a respective housing of a set of housings;
  a set of wires each connected at distal ends to a corresponding one of the set of fasteners, with each individual wire separately connecting one of the set of the fasteners to the ECG monitoring equipment;
  a set of cable corrals each positioned between a pair of the set of housings, with a proximal-most cable corral receiving the entire set of wires and each given cable corral distal to the proximal-most cable corral receiving one fewer of the set of wires than a cable corral proximally-preceding the given cable corral, the cable corrals operating to collect excess wire when a separation between fasteners is reduced and
  wherein shortening or lengthening of a respective cable corral of the set of cable corrals between two adjacent housings of the set of housings changes based upon a shortened or lengthened a distance between the set of fasteners supported by the two adjacent housings of the set of housings and based upon a shortened or lengthened distance between adjacent surface electrodes of the set of surface electrodes, the method comprising:
  (a) attaching each of the set of fasteners to a surface electrode;
  (b) separating the set of fasteners to locate the surface electrodes on a patient while maintaining portions of lengths of the set of wires collected by the corrals.

17. A method of connecting surface electrodes on a patient to ECG monitoring equipment using a harness having:
  a set of fasteners each releasably attachable to a respective surface electrode of a set of electrodes for electrical communication therewith, wherein each of the set of fasteners are supported by a respective housing of a set of housings;
  a set of wires each connected at distal ends to a corresponding one of the set of fasteners, with each individual wire separately connecting a fastener to the ECG monitoring equipment;
  a set of cable corrals each positioned within a respective housing of the set of housings, with a proximal-most cable corral receiving the entire set of wires and each given cable corral distal to the proximal-most cable corral receiving one fewer of the set of wires than a cable corral proximally-preceding the given cable corral, the cable corrals operating to collect excess wire when a separation in distance between fasteners is reduced;
  wherein a shortening or lengthening of a distance between two adjacent cable corrals of the set of cable corrals in the set of housings changes based upon a shortened or lengthened distance between the set of fasteners supported by the set of housings that the two adjacent cable corrals are positioned within, and based upon a shortened or lengthened distance between adjacent surface electrodes of the set of surface electrodes, and wherein the set of cable corrals are rotatable spools, the method comprising:

(a) attaching each of the set of fasteners to a surface electrode;
(b) separating the set of fasteners to locate the surface electrodes on a patient while maintaining portions of lengths of the set of wires collected by the corrals.

\* \* \* \* \*